United States Patent [19]

Moeremans et al.

[11] Patent Number: 4,775,636

[45] Date of Patent: Oct. 4, 1988

[54] BLOT OVERLAY ASSAY USING COLLOIDAL METAL PARTICLES

[75] Inventors: Marc K. J. Moeremans, Mol; Guido F. T. Daneels, Gierle; Jan R. De Mey, Turnhout, all of Belgium

[73] Assignee: Janssen Pharmaceutica N.V., Beerse, Belgium

[21] Appl. No.: 115,652

[22] Filed: Oct. 27, 1987

Related U.S. Application Data

[63] Continuation of Ser. No. 660,832, Oct. 15, 1984, abandoned.

[30] Foreign Application Priority Data

Nov. 25, 1983 [GB] United Kingdom ............... 8331514

[51] Int. Cl.$^4$ ................. G01N 33/553; G01N 33/538
[52] U.S. Cl. .................................... 436/518; 436/525; 436/528; 436/531; 436/805; 436/541; 436/807; 436/824
[58] Field of Search ............... 436/518, 525, 528, 531, 436/805

[56] References Cited

U.S. PATENT DOCUMENTS 4,115,198 9/1978 Coughlin et al. ................. 435/176
4,487,839 12/1984 Kamentsky ........................ 436/518

FOREIGN PATENT DOCUMENTS 7654 5/1979 European Pat. Off. ........... 436/525

OTHER PUBLICATIONS

Gershoniet Al., Analyt. Biochem. 131 (1983) 1–15.
Leuvering et al., J. Immunoassay, 1 (1980) 77–91.

Primary Examiner—Christine M. Nucker
Attorney, Agent, or Firm—Geoffrey G. Dellenbaugh

[57] ABSTRACT

A method for detecting and/or determining an agglomerate formed by the reaction between a specific binding agent and the corresponding acceptor substance according to the general methodology of blot overlay assays by using colloidal metal particles labelled components which may be visualized as a coloured signal at the surface of the blotting medium characteristric for the colloidal metal particles used or quantitatively determined following art-known spectrophotometric procedures such as densitometry.

14 Claims, No Drawings

BLOT OVERLAY ASSAY USING COLLOIDAL METAL PARTICLES

This is a continuation of application Ser. No. 660,832, filed Oct. 15, 1984, now abandoned.

The present invention relates to a method for the detection and/or determination in blot overlay assays of an agglomerate formed by a binding agent and the corresponding acceptor substance. The latter substance is usually contained in an aqueous test sample and becomes at a later stage of the assay adsorbed and/or covalently linked to an immobilizing matrix. Examples of immobilizing matrices are nitrocellulose (NC) film (thin sheets of nitric acid-esterified cellulose of known porosity), diazobenzyl oxymethyl (DBM)- and diazophenylthioether (DPT) modified cellulose paper, paper or cellulose acetate activated with cyanogen bromide, and Nylon based membranes such as Gene Screen and Zetabind. The latter is a nylon matrix (a polyhexamethylene adipamine, referred to as Nylon 66) modified by the introduction of numerous tertiary amino groups during manufacturing. Said immobilizing matrices are commonly referred to as *blotting media*. (See for example J. M. Gershoni and G. E. Pallade, Analytical Biochemistry 131, 1-15, (1983)). Blot overlay assay methods may generally be divided in two different techniques:

A. In the sandwich overlay assay, the purified or enriched specific binding agent is attached to the immobilizing matrix according to B (see below), preferably as a small spot, and the acceptor substance is allowed to bind to it, resulting in immobilization on the matrix of the acceptor substance which can subsequently be detected. Due to the specificity of the specific binding agent, this will allow one to isolate the acceptor substance out of a complex test sample such as urine, plasma, serum, other body fluids, cell free translation systems, cell and tissue lysates, etc ..., and to use this approach for semi-quantitative and/or qualitative (diagnostic) assays: the so-called sandwich blot overlay assay (SBOA). Until now, the practical value of SBOA's is negligible because only relatively complex detection methods are available today. Due to the embodiment of this invention detection is made very simple and the interest in SBOA for diagnostic use may be increased.

B. In the direct blot overlay assay, the acceptor substance is directly attached to a blotting medium by a procedure known as "transferring" or "blotting". Different ways well-known from the literature of achieving this exist. For example, small drops containing a known or unknown amount of acceptor substance (purified or not) in an aqueous solution, of the order of 1 μl (but other volumes apply as well) are spotted on the blotting medium in order to allow the acceptor substance to become attached to the blotting medium. Such dot-blots can potentially be used for the diagnostic detection of the presence of specific binding agents to the immobilized acceptor substance in various body fluids. If the acceptor substance is part of a complex mixture, the latter can first be separated by a variety of chromatographic techniques such as, thin layer chromatography or electrophoretic techniques, for example in polyacrylamide gels, such as sodium dodecyl sulfate (SDS) electrophoresis, iso-electric focusing, 2-D gel electrophoresis, gradient gel and acid-urea gel electrophoresis and non-denaturating gel electrophoresis, in order to facilitate identification of the acceptor substance. In some cases, like for nucleic acids, agar gels can also be used. The electrophoretically resolved components (such as proteins, peptides and nucleic acids) are then transferred to the immobilizing matrix by procedures known as capillary-, vacuum- or electrotransfer (or-blotting). The components are then immobilized on the blotting medium while largely retaining the original electrophoretic pattern. This complete pattern can be visualized with known staining techniques such as amido black and Coomassie blue and the component under investigation (the acceptor substance) can be detected (see further), and its location be related to the whole electrophoretic pattern.

So far, most of the specific binding agents used have been proteins which bind to well-defined domains of the acceptor substance. Lectins are used to detect glycoproteins. Polyclonal and monoclonal antibodies to detect their corresponding antigens or haptens, (e.g. biotin or biotinylated DNA probes with anti-biotin, DNP on dinitrophenylated proteins with anti-DNP). Blot overlay assays are already widely used for testing the specificity of antibodies and for screening of the production of monoclonal antibodies. Besides these widely used systems, many other protein-protein (e.g. calmodulin or actin binding proteins), or protein-ligand (e.g. avidin-biotin) interactions in which one of the components is immobilized can be analyzed. These include DNA-protein and RNA-protein interactions, receptor-ligand interactions, and in general any other macromolecule-macromolecule interactions of sufficient specificity and affinity.

An essential part of the blot overlay assays is the method used for visualizing the immobilized acceptor substance. Direct and indirect techniques exist. The visualization principles make use of markers: radioactive isotopes ($^3$H, $^{14}$C, $^{32}$P, $^{35}$S or $^{125}$I), followed by autoradiographic development; enzymes which can form insoluble coloured products, or fluorochromes. In direct methods, the marker is linked to the specific binding agent. In the indirect method, it is linked to a macromolecule that can specifically bind to the first specific binding agent. If the latter is an antibody, the macromolecule can be protein A or a secondary antibody. More step techniques like the avidin biotinylated horseradish peroxidase complex (ABC) and unlabelled peroxidase anti-peroxidase (PAP) methods can also be used for antibodies.

The essential point of the present invention is the use of a dispersion of a metal or metal compound or nuclei coated with a metal or metal compound as the visualization and/or detection principle in blot overlay techniques. The term "colloidal metal particles" used in the text is meant to include dispersions of particles, optionally a sol, consisting of a metal, a metal compound or nuclei coated with a metal or metal compound.

Colloidal metal particles can be prepared following art-known procedures, such as, for preparing colloidal gold, silver or iron oxide and the like. Colloidal metal particles can be attached directly or indirectly to the specific binding protein or the acceptor substance, or to a macromolecule that binds specifically to the first specific binding agent, for example protein A, secondary antibody (in case of a primary antibody), or streptavidin and avidin (in case one of the components is biotinylated), with retention of most of the original binding activities, following art-known procedures. Under attaching is understood any chemical or physical binding, such as binding via covalent bonds, via hydrogen bridges, polar attraction and adsorption.

It has now been found that when a blotting medium with an acceptor substance attached to it, either indirectly (see A) or directly (see B) is incubated with the appropriate concentration of colloidal metal particle labelled specific binding agent (direct detection method) or first with unlabelled specific binding agent and then with a colloidal metal particle labelled macromolecule that can specifically bind to the first specific binding agent (indirect detection method), colloidal metal particles will accumulate at the specific binding sites and surprisingly become visible as the colour characteristic for the colloidal metal particles used. For example, a pink to dark red colour is obtained when a metal such as gold is used and yellow to brown/black when silver is used. This colour forms a signal that can be qualitatively read with the naked eye or optionally measured with art-known spectrophotometric procedures such as densitometry.

The particle size of the colloidal metal particles are preferably comprised between 3 nm to 100 nm and more preferably between 5 nm and 50 nm.

As examples of colloidal metal particles that can be attached to specific binding agents, the metals platinum, gold, silver and copper, and the metal compounds, silver iodide, silver bromide, copper hydrous oxide, iron oxide, iron hydroxide or hydrous oxide, alumunium hydroxide or hydrous oxide, chromium hydroxide or hydrous oxide, vanadium oxide, arsenic sulfide, manganese hydroxide, lead sulfide, mercury sulfide, barium sulfate and titanium dioxide have been described. It is also known that colloids consisting of nuclei, coated with the above mentioned metals or metal compounds can be used. These particles have similar properties as the metal or metal compound colloids but size, density and metal content can be optimally combined. In general, all colloidal metal particles or metal compounds which can be linked to specific binding agents without destroying their binding activity, and which give a colour intensity in blot overlay assays sufficient to be seen by the naked eye can be used. Preferably the sensitivities are equal or superior to those obtained with gold or silver.

The use of colloidal metal particles, in particular those of gold sols, which are covered on the surface with specific binding agents such as antibodies, lectins, protein A, avidin, and many others, or even acceptor proteins such as antigens is now well established in many cytochemical marking techniques in transmission and scanning electron microscopy. An example of the use of a colloidal metal particle consisting of a polymer coated with a metal is dextran coated iron which, when attached to antibodies, provides a very useful marker for transmission electron microscopy. These uses, however, exploit the typical electron opacity of these markers (transmission EM) or their potential to emit secondary electrons or backscatter primary electrons (scanning EM).

Colloidal metal particles, particularly those made of gold and silver, are also used as markers for light microscopic cytochemical marking techniques after it was shown that accumulations of such colloidal metal particles at binding sites in tissue slides or at cell surfaces could be seen provided that a light microscope was used to look at the preparation.

Colloidal metal particles are also used for certain in vitro qualitative and quantitative determinations of immunological components, such as haptens, antigens and antibodies in an aqueous medium. These techniques have been called sol particle immunoassays, and passive gold agglutination (Geoghegan).

The passive gold agglutination technique is based on the agglutination of a gold labelled antigen (gold particles 18–20 nm) by unlabelled antibody, and involves the use of a standard microtiter set, wherein non-aggregated gold flows down the sides of the wells making a red streak. This technique is analogous to classical passive hemagglutination and is equally sensitive and has been claimed to have potential for reverse agglutination in which it is the antibody which is labelled with gold.

Sol particle immunoassays fall into two categories. The first is called homogeneous sol particle Immunoassay and is based on the agglutination of antibody labelled colloidal particles by immunochemically bi- or multivalent antigens or by haptens coupled to a carrier protein. The agglutination results in colour reduction as measured by colorimetry with buffer as blank. The agglutination of the colloidal metal particles may then be inhibited by free hapten molecules from the sample. Such methods are described in European Pat. No. 0007654.

The second type of sol particle immunoassay is based on bound/free colloidal metal particle conjugate separation methods analogous to radioimmunoassay and enzyme-immunoassay. Such methods are described in European Pat. No. 0007654. One such method is called Sandwich Sol Particle Immunoassay (SSPIA) and is analogous to a sandwich ELISA or solid phase sandwich radioimmunoassay. In a SSPIA typically an antibody against the antigen to be determined is first adsorbed on the surface of a microtitration plate (e.g. made of polystyrene). A sample (antigen standard or blank), dissolved in an appropriate buffer system is pipetted into the wells coated with antibody and incubated appropriately. Gold-labelled antibody is added and the reaction mixture further incubated. The wells are aspirated and washed to remove the unbound conjugate. Finally, the bound immune complex together with the homogenized colloidal metal particles are disengaged. Either the colour intensity of the dispersion obtained is inspected visually or the metal concentration is measured by means of a colorimeter. The visual inspection method (e.g. the colour of the dispersed gold) could only be used at higher antigen concentrations.

It should be noted that sol particle assays have also been descibed to be useful for non-immunological assays, in general "for the detection and/or determination of one or more components of the reaction between a specific binding protein and the corresponding bindable substance in an aqueous test sample, whilst applying the known binding affinity of such components for one another, wherein one or more labelled components are used obtained by coupling directly or indirectly the desired component of said reaction to particles of an aqueous dispersion of a metal, metal compound or polymer nuclei coated with a metal or metal compound, having a particle size of at least 5 nm, whereby during the reaction or after an adequate reaction time, optionally after separation of the bound and free labelled components, the physical properties and/or the amount of the metal and/or the formed metal containing agglomerate is/are determined in the test sample or one of the derived fractions, following art-known procedures, which determination provides a qualitative and/or quantitative indication of the component or components to be detected and/or determined".

The present invention is concerned with the use of colloidal metal particles as markers in blot overlay assay methods which use is entirely novel and has surprisingly proved to be possible.

Colloidal metal particles are meant to include a dispersion of a metal, metal compound or nuclei coated with a metal or metal compound.

The use of colloidal metal particles as markers applies to all forms of blot overlay assays and introduces the advantage that colloidal metal particles accumulating at the binding sites at the surface of the blotting medium become directly visible by the naked eye with a sensitivity at least comparable with the very high sensitivity of existing techniques such as enzyme based blot overlay assays. It is stressed that the invention would not have practical value if the last point could not be included. It has the important advantage that the assay can be read without the need for a secondary enzymatic reaction, autoradiography or viewing system for fluorescent dyes, or for a disengagement of the bound colloidal metal particles for subsequent measurement with the naked eye (low sensitivity), colorimetry or CRAAS (higher sensitivity) like in the sandwich sol particle immunoassays. Its major advantage is its simplicity, because the colour develops during the reaction. This makes it possible to stop the reaction when the desired signal is produced, or to calibrate the system in order to obtain a predetermined result within a fixed time limit.

The use of gold labelled antibodies is much simpler than and as sensitive as a reputedly very sensitive immunoperoxidase method. This simple assay can be used for a test kit to indirectly detect the presence of specific binding agents to an acceptor substance which is attached to the blotting medium, and a colloidal metal particle labelled specific binding agent for the first specific binding agent. If the specific binding agent is an antibody, this can be colloidal metal particle labelled secondary antibody or protein A. This could be worked out as a very simple dip stick test, for example a spot blot overlay immunoassay for the rapid screening of the presence of antibodies to a selected antigen in an aqueous test sample such as serum.

The process comprises the subsequent steps of:
i. Immobilizing the acceptor substance to an immobilizing matrix, known as blotting medium.
  i.i. Either by direct adsorption and/or covalent binding generally called blotting, optionally after applying a procedure of electrophoretic separation and applying a procedure of transfer or blotting from the electrophoretic medium to the blotting medium and subsequently quenching remaining protein binding sites following art-known procedures such as use of BSA, gelatine, PEG or Tween 20.
  i.ii. Or by allowing the acceptor substance to become bound by a specific binding agent which has become immobilized to the blotting medium by contacting said blotting medium with an aqueous solution which contains the acceptor substance.
ii. Contacting the blotting medium of (i) for a given time, after which it is washed and air-dried, with:
  ii.i. Either colloidal metal particle labelled specific binding agents, at an appropriate concentration.
  ii.ii. Or first unlabelled specific binding agent at an appropriate concentration and then a colloidal metal labelled protein specific for the unlabelled specific binding agent.
iii. Reading the coloured signal produced by and characteristic for the bound colloidal metal particles at the surface of the blotting medium with the naked eye or using art-known spectrophotometric techniques such as densitometry.

This invention is also related to test kits to be used for the direct or indirect determination of one of the components of the reaction between a specific binding agent and the corresponding acceptor substance in a blot overlay assay containing: a colloidal metal particle labelled component which has been obtained by coupling a component of said reaction or a component that can be used to detect this reaction indirectly to colloidal metal particles as defined above and other reagents. If the reaction is of the immunological type, the test kit can be used for sandwich blot overlay assays (see example III) and for the determination of the presence of antibodies in serum against selected antigens (see example I).

An optional feature of the present invention makes use of the fact that the detection of the colloidal metal particles bound at the surface of the blotting medium, as the result of a blot overlay assay, can also be visualized indirectly and/or enhanced by applying a physical developer which can be reduced to the corresponding metals. Suitable physical developers are, for example, silver lactate, silver nitrate and the like. For example, when silver is used as physical developer, the reaction initially takes place at the surface of the metal particles which catalyse the reduction, and becomes subsequently auto-catalytic on these seeds. It results in the formation of a black, highly contrasting signal, provided by the accumulation of metallic silver. This provides a considerable increase in sensitivity. In order to obtain light-insensitive silver precipitates, we have also discovered that the blots have to be fixed with a fixative used for micrograph prints.

Physical developers have been used for many years for the visualization of water insoluble metals, especially metal sulfides in tissues (see Danscher, Histochemistry 71, 1-16, 1981). The metal sulfides and metallic silver have a catalytic effect on the reduction of silver ions. Colloidal gold metal in tissue can also be demonstrated with a physical developer and this has been exploited by Holgate et al. (J. Histochem. Cytochem. 31, 938-944, (1983)) for the introduction of the immunogold/silver staining method, which results in a sensitivity much superior to the original immunogold staining method.

The major advantage of the optional feature of this invention lies in its enormous sensitivity which exceeds that of any other existing detection method for blot overlay assays. It can be used when the user wants to economise on the quantity of reagents used, or when extremely low amounts of acceptor substance and/or specific binding agent are available.

An additional optional feature of the present invention is the use of a photographic fixer, decreasing the background and improving the stability of the reaction product of the physical developer.

The following examples are intended to illustrate and not to limit the scope of the present invention.

EXAMPLES

Example I

A simple spot blot overlay immunoassay for the indirect demonstration of antibodies to dog brain tubulin and calmodulin with gold labelled secondary antibodies in serum of immunized rabbits.

I.1 Preparation of the antisera

1.1 Raising of antisera

One mg dog brain tubulin (extracted from SDS-polyacrylamide gels) in 1.0 ml buffer (0.1M Pipes, pH 6.9) or one mg of electrophoreticallypure dog brain calmodulin (in $H_2O$) was mixed with 1.0 ml complete Freund's adjuvans (DIFCO). After homogenization the antigen was injected intradermally at five sites along the spine of white rabbits. Booster injections were given every four weeks. Antigen was prepared in the same way except that incomplete Freund's adjuvans was used. One week, after each booster, rabbits were bled ($\pm$60 ml blood was taken), serum was prepared and stored in aliquots at $-20°$ C. until use.

1.2 Colloidal gold labelled secondary antibodies

These were purchased from Janssen Life Sciences Products, 2340 Beerse, Belgium. Code: GAR G20. These are affinity-purified goat antibodies to rabbit IgG, labelled with 20 nm colloidal gold particles.

Preparation of nitrocellulose paper strips with antigen containing spots

Ten 1 $\mu$l drops of 4-fold serial dilutions (starting at 250 ng/$\mu$l) of pure tubulin in 0.1M PIPES, 1 mM EGTA, 1 mM $MgCl_2$, pH 6.75 or pure calmodulin in $H_2O$, were spotted as a row on dry nitrocellulose strips (6 cm$\times$0.6 cm). When the spots were dried (approximately 5 minutes) remaining protein binding sites on the strips were quenched by incubating them with a solution of 5% bovine serum albumin (BSA) in 20 mM Tris buffered saline, pH 8.2 for 30 min at 37° C.

1.3 Test protocol for the detection of tubulin and calmodulin antibodies. Comparison of the use of gold labelled antibodies with the ABC-peroxidase detection method The buffer used throughout the procedure was 0.1% BSA Tris (0.1% BSA in 20 mM Tris-HCl, 0.9% NaCl pH 8.2, 20 mM $NaN_3$), unless otherwise stated.

a. Incubation with primary antiserum 2 strips were incubated in stoppered 5 ml plastic tubes with 1 ml rabbit anti-tubulin serum, 1:1000 diluted in 0.1% BSA-Tris for 2 hours at room temperature.

2 strips were incubated as above with the same antiserum absorbed on tubulin covalently linked to Sepharose-4B to serve as a control for antigen specificity.

2 strips were incubated as above with 1 ml rabbit anti-calmodulin serum, 1:1000 diluted in 0.1% BSA-Tris, for 2 hours at room temperature.

2 strips were incubated as above with the same absorbed on calmodulin, covalently linked to sepharose-4B. After incubation with the absorbed and non-absorbed primary antisera the strips were washed 3$\times$10 minutes in 0.1% BSA-Tris. One strip of each couple was further incubated with GAR G20, (see 1.3.b). The other was incubated with the very sensitive Vectastain ABC immunoperoxidase kit, purchased from Vector Laboratories and used according to the instructions of the manufacturer, (see 1.3.c).

b. Incubation with gold labelled secondary antibody: GAR G20

The washed strips (see 1.3.a) were incubated with GAR G20, diluted at $O.D._{520 nm}^{1 cm}=0.2$ in 0.1% BSA-Tris+0.4% gelatin, for 2 hours. After this incubation the strips were washed in 0.1% BSA-Tris for 2$\times$10 minutes and air-dried.

c. Incubation with the Vectastain kit

The washed strips (see 1.3.a) were incubated with secondary biotinylated antibody solution (1:200 in 0.1% BSA-Tris) for 1 hour. The strips were washed in an excess 0.1% BSA-Tris for 3$\times$10 minutes and then incubated in the avidin-biotinyl peroxidase complex for 1 hour. The complex was prepared according to the instructions of the manufacturer: 100 $\mu$l of reagent A (avidin DH) was added to 10 ml PBS (Dulbecco's, without $Mg^{2+}$ and $Ca^{2+}$). 100$\mu$l of reagent B (biotinylated horseradish peroxidase) was added while continuously stirring. The complex was used after five minutes. The strips were washed in 0.1% BSA-Tris (2$\times$10 minutes) and subsequently in 100 mM Tris-HCl buffer, pH 7.6. The immobilized peroxidase was then visualized with 4-chloro-1-naphtol as the substrate: 20 mg 4-chloro-1-naphtol was dissolved in 1 ml ethanol and further diluted with 20 ml 100 mM Tris-HCl buffer pH 7.6, warmed to approximately 50° C. 200 $\mu$l $H_2O_2$ 1% was added, and the substrate solution added with a syringe to the strips through a microfilter (0.2$\mu$, millipore) mounted on the syringe. The reaction was allowed to proceed for 5 minutes and the reaction stopped by washing the strips with $H_2O$ and air-drying.

1.4 Evaluation

In the ABC-procedure, positivity is detected as a blue colour. When colloidal gold is used, the positivity is pink-reddish, for the size of gold used (larger gold particles, e.g. 40 nm give a purplish colour). The sensitivity for both methods is entirely comparable and is of the order of 5 ng/$\mu$l for tubulin and 30 ng/$\mu$l for calmodulin, under the conditions used. The specificity is shown by the negative reaction when the antisera are adsorbed with their respective antigen.

Example II

Screening for the presence of monoclonal mouse antibodies to microtubule associated proteins in culture supernatants of growing hybridomas, using gold labelled goat antibodies to mouse IgG.

2.1 Immunization of mice

Mice (Balb/C) were injected with a homogenized mixture (see example 1.1.) of rat brain microtubule proteins (100 $\mu$g/mouse) (prepared by two cycles of temperature-dependent polymerization-depolymerization) and complete Freund's adjuvans. Injections were given subcutaneously at five sites on the back. Booster injections of antigen (100 $\mu$g) prepared with incomplete Freund's adjuvans were given 3 times fortnightly. Three days before fusion of the spleen cells with the myeloma cell line, mice were boosted by intravenous injection of 50 $\mu$g antigen/mouse in 100 $\mu$l PBS-buffer.

2.2 Fusion of spleen cells with NS-1 myeloma cells

NS-1 cells were fused with spleen cells of two immunized mice according to art-known procedures and the resulting hybridomas were cultured in five 96-well plates (Nunc) at 37° C. in a water saturated atmosphere containing 7% $CO_2$. After about 2 weeks of growth, 100 μl of the culture supernatant of wells containing growing hybridomas was taken and tested for the presence of secreted monoclonal antibodies (see 2.4).

2.3 Preparation of nitrocellulose paper strips onto which a pattern of proteins from an SDS-polyacrylamide gel has been electroblotted SDS-polyacrylamide gel electrophoresis of the antigen (2×polymerized microtubule proteins) was carried out according to Laemmli, on a 7.5% gel. The antigen dissolved and boiled in sample buffer was loaded on top of the stacking gel as a continuous layer, 300 μg per gel. When the dye front had migrated 3 cm into the separating gel, electrophoresis was stopped. A small vertical strip of the gel was cut off for coomassie blue staining and the remainder was used for electroblotting on nitrocellulose paper. The gel was equilibrated in transfer buffer [25 mM Tris-192 mM glycine/20% (Vol/Vol) methanol at pH 8.3], for 30 minutes at room temperature. The gel was put on a nitrocellulose sheet (presoaked in buffer) and care was taken to avoid or remove all trapped air bubbles. This was sandwiched between two presoaked filter papers and two nylon screen cushions. This resulted in a tight fit in a closed electrode grid of an EC-electroblot apparatus in which electroblotting was carried out overnight at 400 mA at room temperature. After electrophoretic transfer remaining protein binding sites on the nitrocellulose paper sheet were quenched by incubating the sheets in 5% BSA in 20 mM Tris buffered saline, pH 8.2, for 30 minutes at 37° C. The nitrocellulose sheet was subsequently cut into 3 mm wide strips, parallel to the direction of electrophoresis. These strips were used for screening the supernatants of hybridoma cells.

2.4 Detection of monoclonal antibodies

100 μl of each hybridoma culture supernatant was transferred into 3.5 cm long 0.5 ml Eppendorf tips and diluted 1:5 with 0.4 ml 0.1% BSA-Tris. The tips and strips were provided with a code nr. Each tip received one strip and these were incubated for 2 hours. The strips were washed batch-wise in an excess 0.1% BSA-Tris and also incubated batch-wise with GAM G20 (goat anti-mouse IgG, labelled with 20 nm colloidal gold particles) purchased from Janssen Life Sciences Products, 2340 Beerse, Belgium. The GAM G20 was diluted with 0.1% BSA-Tris+0.4% gelatin to an $O.D._{520\ nm}^{1\ cm} = 0.1$ and reacted overnight. The strips were washed with 0.1% BSA-Tris and $H_2O$ and air-dried.

Positivity was clearly visible as pink to reddish bands (see enclosed examples), corresponding to protein bands with a given molecular mass. This very simple screening procedure not only identifies antibody secreting hybridomas, but gives immediate information on the specificity of the concerned antibody and is therefore of great help for selection of interesting antibody secreting hybridomas.

Example III

A sandwich immuno-blot overlay assay for the detection of antigens in an aqueous test sample: the detection of IgG's in an aqueous test sample.

3.1 Principle of the assay

A small drop (±1 μl) of a purified or enriched antibody monospecific for the antigen to be determined is blotted on a strip of nitrocellulose paper (or any convenient blotting medium) dried, and free protein binding sites quenched (see example 1.3.). Optionally these antibody containing, quenched strips can be washed in water, air-dried and stored. This strip is then incubated with a volume of antigen containing test solution, during a fixed time. After washing off non-bound substances the strips are further incubated with appropriately diluted colloidal metal particle (for example a sol of gold or silver) labelled monospecific antibody, similar to the one adsorbed onto the blotting medium. Optionally, two monoclonal antibodies, each recognizing a different antigenic epitope can be used. One is attached to the blotting medium, the other is attached to colloidal metal particles. Under fixed conditions, the assay will be able to detect a predetermined minimal concentration of antigen and can be used as a qualitative diagnostic test, provided it can detect a minimally required concentration in a given test solution.

3.2 Example of the principle: the detection of rabbit IgG's in a buffered solution of rabbit IgG of known concentration To test the feasibility of the principle of this new sandwich assay, the following experiment was done:

6 strips of 6×0.6 cm of nitrocellulose paper were blotted with drops (1 μl) containing decreasing amounts (⅓ dilution series starting at 125 ng/μl) of affinity purified goat antibodies to rabbit IgG (GAR IgG) as described in example 1.2.

Remaining protein binding sites were quenched as described in example 1.2. 1 strip (No. 6) was washed in 20 mM Tris-buffer saline, blotted dry on filter paper, air-dried and used after dry overnight storage at room temperature.

The remaining five strips were incubated in stoppered plastic tubes for 30 minutes at room temperature as follows:

No. 1: with RIgG, 1 ml, 1 μg/ml
No. 2: with RIgG, 1 ml, 0.25 μg/ml
No. 3: with RIgG, 1 ml, 0.063 μg/ml
No. 4: with RIgG, 1 ml, 0.015 μg/ml
No. 5: wIth RI&G. 1 ml, 0 μg/ml The rabbit IgG was diluted in 0.1% BSA-Tris. The strip No. 6 was incubated with 0.25 μg/ml RIgG.

The strips were washed 2×10 minutes in 0.1% BSA-Tris.

All the strips were incubated for exactly 1 hour at room temperature in GAR G20 (goat antibodies to rabbit IgG, labelled with colloidal gold particles of 20 nm diamater) purchased from Janssen Life Sciences Products, B-2340 Beerse, Belgium. The GAR G20 was diluted at an $O.D._{520\ nm}^{1\ cm} = 0.2$ with 0.1% BSA-Tris+0.4% gelatine.

The strips were washed with 0.1% BSA-Tris, then with water and air-dried.

3.3 Evaluation

Spots containing as little as 15 ng adsorbed GAR IgG, become visible as pink dots after incubation for only 30 minutes in 1 ml of a solution containing 15 ng/ml RIgG followed by incubation with 1 ml of GAR G20, 0.0520 nm=0.2 for one hour. Solutions containing at least this amount of RIgG would have been quoted positive. The result of strip No. 6 is identical with that of strip No. 2, indicating that the strips can be dried after the quenching step, with retention of antibody activity.

Example IV

Direct detection of an antigen attached to NC paper with colloidal silver labelled primary antibody: detection of spots of mouse IgG's with colloidal silver labelled goat antibodies to mouse IgG.

NC paper strips (6 cm×0.6 cm) were blotted with spots of mouse IgG (1 µl) containing a two-fold serial dilution from 250–0.4 ng/µl, as described in example 1.2.

The remaining protein binding sites were quenched as in example 1.2.

The strips were incubated with colloidal silver labelled goat antibodies to mouse IgG (purchased from E.Y. Laboratories, SP-0011), diluted 1:100 in 0.1% BSA-Tris, for 1 h 30 min, at room temperature.

The strips were washed 2×10 minutes with 0.1% BSA-Tris $H_2O$ and air-dried.

Positive spots were characterized by a yellow colour. Under these conditions, ±30 ng in 1 µl spot could be detected.

Example V

Testing the specificity of an affinity-purified rabbit antibody to chicken gizzard actin for actin occurring in a total cell lysate of secondary cultures of chicken embryonic lung epithelial cells, using a blot overlay immunoassay and gold labelled secondary antibody followed by silver enhancement.

5.1 Preparation of anti-actin antiserum

Electrophoretically pure chicken gizzard actin was homogenized and injected in rabbits as described for tubulin and calmodulin in example 1.1. Serum was prepared and stored as described in example 1.1.

5.2 Affinity purification of the antibody to actin

Actin was coupled to Sepharose-4-B-CNBr (Pharmacia) according to the instructions of the manufacturer. The antibody was purified directly from serum. The latter was incubated with the antigen containing gel. 20 ml serum for 10 mg coupled antigen was used. After two hours of incubation, the gel was poured into a column and washed with 10 mM Tris-buffered saline (TBS) until the O.D. at 280 nm was almost zero. Non-specifically adsorbing material was eluted with TBS containing 1M NaCl, followed by washing with TBS. The specific antibody was eluted with 0.1M glycine-HCl buffer at pH 2.8. One ml fractions were immediately neutralized with 100 µl M Tris-HCl buffer, pH 8.5. Antibody concentration was measured at 280 nm using an $E_{1\%}=14.3$. Aliquots of the eluted antibodies were stored at −20° C., without further treatment.

5.3 Culture of embryonic chicken lung epithelial cells

Embryonic chicken lung epithelial cells were isolated from 14-day old chicken embryo lungs. The tissue was chopped by hand and trypsinized in 0.25% trypsin in $Ca^{2+}$ and $Mg^{2+}$ free Hanks balanced salt solution at 37° C. for 20 minutes. The reaction was stopped with medium and 10% FCS. After centrifugation and resuspension the cells were transferred into a 75 $cm^2$ T-flask and allowed to attach for 12–24 hours before the medium was changed. After 3–5 days in culture, the cells were briefly (2–3 minutes) trypsinized (in 0.25% trypsin solution) and plated on 9 cm φ petri dishes and used after 3–5 days in culture when the cells were confluent. The cells were grown in Eagle's minimum essential medium supplemented with non-essential amino acids and 10% fetal calf serum, and in a humidified 5% $CO_2$/air athmosphere at 37° C.

5.4 Preparation of total cell SDS-lysate of embryonic chicken lung epithelial cells Cells grown in 9 cm φ petri dishes were washed in $Ca^{2+}$, $Mg^{2+}$ free PBS (Dulbecco's) and collected with a rubber police-man, and immersed in absolute acetone at −20° C., in Eppendorf tip (1.5 ml). The acetone was evaporated and the dry cell residue dissolved in boiling SDS-sample buffer, containing 1 mM TAME (a protease inhibitor). Insoluble residues after centrifugation were discarded. SDS gels (according to Laemmli) were run of this lysate serially diluted with sample buffer and stained with coomassie blue, to estimate the most appropriate dilution of the sample. 1:16 was used for the subsequent electrophoretic transfer to a Gene screen membrane (purchased from NEN). One transfer unit was formed by one lane of such a diluted lysate and one lane of a mixture of purified reference proteins: Ch.g. filamin, Ch.g. myosin (H+L chain), Ch.g. α-actinin, BSA, rat brain tubulin, pig stomach tropomyosin, each at 0.06 µg per lane. The buffer front was now allowed to reach the bottom of the gel and electrophoretic transfer to the gene screen membrane was performed exactly as in example 2.3. The blot unit was cut out and the remaining protein binding sites were quenched as described in example 1.2 and 2.3. Incubation with antibody to actin (0.5 µg/ml) and GAR G20 (O.D. 520 nm=0.2) and dilution of GAR G20 with 0.1% BSA-Tris+0.4% gelatine was carried out in sealed plastic bags of ± the size of the sheet, for 2 hours each, in the same way as described in example 2.4.

After 2 hours incubation with GAR G20, the sheets were washed with 0.1% BSA-Tris and prepared for silver enhancement. At this time a pink-reddish band with the mobility of actin, in the lysate, and corresponding with actin in the protein mixture was already visible.

5.5 Silver enhancement

The sheets were washed for 2 minutes in 1:10 diluted citrate stock buffer. This buffer contains for 100 ml 25.5 g trisodium citrate and 23.5 g citric acid for a pH of 4.

The sheets were then incubated for 15 minutes, carefully protected from light in physical developer containing:

60 ml deionized $H_2O$
0.85 g hydroquinone in 15.0 ml deionized $H_2O$
10 ml citrate buffer pH 4
0.11 g silver lactate in 15.0 ml deionized $H_2O$ The silver lactate is carefully protected from light and added to the other components just before use.

After the reaction time the sheets are washed in excess H₂O and treated with Agefix (1:4 in H₂O), a photographic fixer.

The sheets were again washed in excess H₂O and air-dried.

5.6 Result

The band that was previously visible as pink-reddish coloured bands are now deeply black. The antibody to actin can be considered as extremely specific and has given satisfactory results for immunocytochemical staining of actin containing structures in the cultured cells.

5.7 Conclusion

This silver enhancement strongly increases the contrast and sensitivity of the detection method. For instance the example IV, stained with colloidal silver labelled antibodies was further developed and after only five minutes of reaction, the detection limit was 3 instead of 30 ng/spot.

What we claim is:

1. A process for detecting or determining an acceptor substance in a blot overlay assay comprising the steps of:
   (i) immobilizing the acceptor substance to a blotting medium;
   (ii) contacting said blotting medium with colloidal metal particle labelled specific binding agent for said acceptor substance; and
   (iii) detecting the colored signal on the surface of the blotting medium caused by the colloidal metal particles at the reaction site between said acceptor substance and said specific binding agent.

2. A process according to claim 1 wherein the immobilization-step is effected by direct adsorption or covalent binding after applying a procedure of electrophoretic separation and applying a procedure of transfer or blotting from the electrophoretic medium to the blotting medium and subsequently quenching remaining agent specific binding sites.

3. A process according to claim 1 wherein the immobilization-step is effected by allowing the acceptor substance to become bound by a specific binding protein which has become immobilized to the blotting medium, by contacting said blotting medium with an aqueous solution which contains the acceptor substance.

4. A process according to any one of claims 1-3 wherein the colloidal metal particles consist of gold, silver, platinum, compounds of these metals, or iron or copper compounds having a particle size comprised between 3 nm and 100 nm.

5. A process according to any one of claims 1-3 wherein the colloidal metal particles consist of gold or silver having a particle size comprised between 3 nm and 100 nm.

6. A process according to claim 1 wherein the colloidal metal particles consist of gold or silver having particle size comprised between 3 nm and 100 nm and the final detection of the colloidal metal particles is effected after applying a physical developer.

7. A process according to claim 6 wherein the physical developer is a silver-containing compound.

8. A process for detecting or determining an acceptor substance in a blot overlay assay comprising the steps
   (i) immobilizing the acceptor substance to a blotting medium;
   (ii) contacting said blotting medium with an unlabeled specific binding agent for said acceptor substance and, subsequently, colloidal metal labelled protein specific for the unlabeled specific binding agent; and
   (iii) detecting the colored signal on the surface of the blotting medium caused by the colloidal metal particles at the reaction site between said acceptor substance and said specific binding agent.

9. A process according to claim 8 wherein the immobilization-step is effected by direct adsorption or covalent binding after applying a procedure of electrophoretic separation and applying a procedure of transfer or blotting from the electrophoretic medium to the blotting medium and subsequently quenching remaining agent specific binding sites.

10. A process according to claim 8 wherein the immobilization-step is effected by allowing the acceptor substance to become bound by a specific binding protein which has become immobilized to the blotting medium, by contacting said blotting medium with an aqueous solution which contains the acceptor substance.

11. A process according to any one of claims 8-10 wherein the colloidal metal particles consist of gold, silver, platinum or compounds of these metals, or iron, or copper compounds having a particle size comprised between 3 nm and 100 nm.

12. A process according to any one of claims 8-10 wherein the colloidal metal particles consist of gold or sivler having a particle size comprised between 3 nm and 100 nm.

13. A process according to claim 8 wherein the colloidal metal particles consist of gold or silver having a particle size comprised between 3 nm and 100 nm and the final detection of the colloidal metal particles is effected after applying a physical developer.

14. A processs according to claim 13 wherein the physical developer is a silver-compound compound.

* * * * *